(12) United States Patent
Chaudhary

(10) Patent No.: US 8,778,873 B2
(45) Date of Patent: *Jul. 15, 2014

(54) PARENTERAL COMBINATION THERAPY FOR INFECTIVE CONDITIONS WITH DRUG RESISTANT BACTERIUM

(75) Inventor: Manu Chaudhary, Haryana (IN)

(73) Assignee: Venus Remedies Limited, Panchkula-Haryana (IN)

( * ) Notice: Subject to any disclaimer, the term of this patent is extended or adjusted under 35 U.S.C. 154(b) by 182 days.

This patent is subject to a terminal disclaimer.

(21) Appl. No.: 13/095,665

(22) Filed: Apr. 27, 2011

(65) Prior Publication Data

US 2011/0257079 A1     Oct. 20, 2011

Related U.S. Application Data

(63) Continuation of application No. 11/816,179, filed as application No. PCT/IN2006/000044 on Feb. 8, 2006, now Pat. No. 7,960,337.

(30) Foreign Application Priority Data

Feb. 14, 2005   (IN) .............................. 308/DEL/2005

(51) Int. Cl.
 *A61K 31/546* (2006.01)
 *A61K 45/06* (2006.01)

(52) U.S. Cl.
 USPC .......................................................... 514/2.9

(58) Field of Classification Search
 None
 See application file for complete search history.

(56) References Cited

U.S. PATENT DOCUMENTS 6,660,267 B1 * 12/2003 Carroll ....................... 424/181.1
6,900,184 B2    5/2005 Cohen et al.
2003/0083231 A1 * 5/2003 Ahlem et al. ..................... 514/2

OTHER PUBLICATIONS

Arias et al., J. of Chemotherapy, 2001, vol. 13, pp. 535-540.*
Climo et al., Antimicrobial Agents and Chemotherapy, 1999, pp. 1747-1753.*
Huebner et al., S. Afr. Med., 2000, pp. 1116-1121.*
Desbiolles et al., Antimicrobial Agents and Chemotherapy, 2001, pp. 3328-3333.*
Wright, D., et al., "In Vitro Inactivation of Aminoglycosides by Cephalosporin Antibiotics", "Arch. Pathol. Lab. Med.", 1988, pp. 526-528, vol. 112.

* cited by examiner

Primary Examiner — Karlheinz R Skowronek
Assistant Examiner — Roy Teller
(74) Attorney, Agent, or Firm — Hultquist, PLLC; David Bradin

(57) ABSTRACT

The invention describes a pharmaceutical composition to combat multiple-drug-resistant bacteria in non-ocular infective conditions. Compositions comprising glycopeptides, in particular vancomycin, and cephalosporins, in particular ceftriaxone, are disclosed. Such compositions are found to be useful for parenteral administration for hospitalized patients with serious infections. Specifically, this invention also discloses a pharmaceutical composition further including an excipient such as CVMC agent and is available in dry powder form for reconstitution before injection with a suitable solvent. The pharmaceutical compositions of this invention have been found normally to enhance resistance to precipitation in solutions to be administered parenterally. The invention also gives details of the dosage forms stored in sealed containers to be reconstituted before use. The invention further provides a process to manufacture these compositions and also a method of treating a subject having non-ocular infective conditions due to multi drug resistant bacterium.

16 Claims, No Drawings

PARENTERAL COMBINATION THERAPY FOR INFECTIVE CONDITIONS WITH DRUG RESISTANT BACTERIUM

CROSS-REFERENCE TO RELATED APPLICATIONS

This continuation application claims priority of U.S. patent application Ser. No. 11/816,179 filed Aug. 14, 2007 now U.S. Pat. No. 7,960,337, which was published as U.S. Patent Application Publication No. 2008/0188403 on Aug. 7, 2008 which in turn claims priority of International Patent Application No. PCT/IN2006/000044 filed on Feb. 8, 2006, which in turn claims priority of Indian Patent Application No. 308/DEL/2005 filed Feb. 14, 2005. The disclosures of all such applications are hereby incorporated herein by reference in their respective entireties, for all purposes.

FIELD OF THE INVENTION

The present invention relates to a pharmaceutical composition as a method of treatment of non-ocular infective conditions for use against multi drug resistant bacteria. The particular of the invention discloses a pharmaceutical composition containing two different antibiotics, a glycopeptide and a cephalosporin, combined with the help of at least one solubilizing/stabilizing agent and is present in dry powder form. The method of treatment disclosed by the invention follows a parenteral route of administration after reconstitution with a suitable solvent.

BACKGROUND OF THE INVENTION

Use of antibacterial agents has grown rapidly over the past few years and so has the resistance of bacterial strains to antibiotics that use these agents as detailed by Sharma Rashmi et al; Indian J Med Sci 2005 in their article: "Antibacterial resistance: Current problems and possible solutions". New range of bacterial strains that are resistant to multiple drugs has also evolved.

Penicillin, which is the first known antibiotic, has exhibited an excellent efficacy toward Staphylococci. However, penicillin resistant bacteria that degrade penicillin, emerged with the period of time. Research and development of penicillinase resistant penicillins (PRP) such as methicillin and cephems antibiotics provided solutions in clinical aspects to many problems posed by the penicillin resistant bacteria.

However, in recent years, as a result of overuse and misuse of third-generation cephem antibiotics, which have weak antibacterial potency on staphylococci and which are resistant to these antibiotics have selectively proliferated. Such bacteria have come to spread in hospitals, leading to rise in number of cases of hospital acquired infections. In particular, methicillin-resistant Staphalococcus aureus bacteria, commonly known as MRSA, has emerged, against which all known beta-lactam agents are ineffective. MRSA is an example of multiple-drug-resistant bacteria that are broadly resistant to not only penicillin antibiotics but also cephem antibiotics and aminoglycoside antibiotics individually. Examples of currently used antibiotics against MRSA infections include formulations containing glycopeptides such as vancomycin (VCM) and the like. However, VCM is involved in resistance to bacteria such as MRSA as discussed in 'Emergence of low level vancomycin resistance in MRSA' by Assadullah S et al 2003.

In addition, combinations of multiple antibiotics have been conventionally investigated aiming at the enhancement of antibacterial potency in an article 'Re-emerging Staphylococci Infections' by Barry Kreiswirth. Therefore, there exists an urgent need to the development of novel antibacterial combination drugs which are effective on resistant bacteria and can act synergistically as is done in the invention.

There have been many attempts to combat broad-spectrum gram negative and gram positive bacteria. These include administration of multiple antibacterial agents such as vancomycin and ceftriaxone. Ceftriaxone is less active against gram positive cocci than first generation cephalosporin. However, it is markedly active against gram negative bacteria such as Enterobacteriaceae including beta lactamase producing strains and penicillin resistant strains such as Haemophilus influenzae, Neisseria gonorrhoeaea and N. meningitis. It is also active against Staphylococcus aureus including penidllinase producing strains but not against methicillin resistant Staphylococcus aureus. Whereas vancomycin acts against variety of gram positive bacteria including methicillin resistant Staphylococcus aureus and Staph. epidermidis. Vancomycin shows high level acquired transferable resistance against Enterococci which appears to be plasmid mediated.

The use of multiple antibacterial agents for prevention and treatment of a variety of infectious disease states are found to be synergistic in vitro Ribes S et al J Antimicrob Chemother 2005 in their article explained that an additive effect was observed when combinations of ceftriaxone plus vancomycin were studied at sub inhibitory concentrations.

The emergence of multidrug-resistant pneumococci and, more recently, of pneumococci tolerant to vancomycin are important public health concerns worldwide (Henriques Normark et al, Clin. Infect. Dis. 2001; Novak, R, Nature 1999; R. M. Atkinson et al 40th Intersci. Conf. Antimicrob. Agents Chemother., 2000; A. Marchese, et al 40th Intersci. Conf. Antimicrob. Agents Chemother., 2000).

Various earlier investigations show that combination of vancomycin and ceftriaxone is more active against bacteria than monotherapy alone against commonly encountered pathogens in bacterial meningitis. Violeta Rodriguez-Cerrato, Antimicrob Agents Chemother. 2003; the aims of their study were to assess the bacteriologic effectiveness of these agents against experimental meningitis caused by vancomycin tolerant pneumococci and to compare the results with those obtained by conventional therapy with vancomycin and ceftriaxone in combination.

Rifampicin+ceftriaxone versus vancomycin+ceftriaxone in the treatment of penicillin- and cephalosporin-resistant pneumococcal meningitis in an experimental rabbit model' by Suntur B M et al in Int J Antimicrob Agents. 2005 found Ceftriaxone+rifampicin was as effective as ceftriaxone+vancomycin.

Kaplan S L (2002) found that ceftriaxone and vancomycin are useful in the treatment and management of pneumococcal meningitis. Kaplan mentions that the standard empiric therapy for suspected bacterial meningitis for infants and children older than 1 month of age is the combination of cefotaxime or ceftriaxone and vancomycin. Treatment is modified after antimicrobial susceptibilities are available.

Jaing, T H, et al, in their 2002 publication reported a treatment of meningitis caused by highly-penicillin-resistant Streptococcus mitis in a leukemic child. The paper reported the case of a patient that was successfully treated with a combination of vancomycin, ceftriaxone, and granulocyte-colony-stimulating factor.

Cottangnoud P et. al. (2002) found that in experimental rabbit meningitis, cefepime given at a dose of 100 mg/kg was associated with concentrations in the cerebrospinal fluid of between 5.3 and 10 mg/L and a bactericidal activity of −0.61+/−0.24 Delta log(10) cfu/mL×h, similar to the standard regimen of ceftriaxone combined with vancomycin (−0.58+/−0.14 Delta log(10) cfu/mL×h) in the treatment of meningitis due to a penicillin- and quinolone-resistant pneumococcal mutant strain (MIC 4 mg/L).

Banon et. al. (2001) worked on time-kill evaluation in Spain. In this study the bactericidal activity of four antimicrobial regimens against ten clinical isolates of S. pneumoniae (five with an intermediate resistance to penicillin and five highly resistant ones), was determined by means of kill kinetics studies using either penicillin, or ceftriaxone, in combination with vancomycin, or fosfomycin.

Desbiolles et. al (2001) worked on fractional maximal effect method for in vitro synergy between amoxicillin and ceftriaxone, and between vancomycin and ceftriaxone, against Enterococcus faecalis and penicillin-resistant Streptococcus pneumoniae. They reported an assessment of the use of a new in vitro testing method and graphical representation of the results to investigate the potential effectiveness of combinations of amoxicillin (AMZ) plus ceftriaxone (CRO), and of CRO plus vancomycin (VAN) against strains of Streptococcus pneumoniae (PRP strains) highly resistant to penicillin and cephalosporins. Consequently, either of the combinations was proposed for use for the treatment of PRP infections.

Huebner et. al. (2000) reported that ceftriaxone or cefotaxime should be used in combination with vancomycin for the treatment of meningitis until a cephalosporin-resistant pneumococcal cause is excluded.

Roos (1999) studied bacterial meningitis therapy using a combination of third generation cephalosporins and vancomycin. He has suggested that initial empiric therapy for community-acquired bacterial meningitis should be based on the possibility that penicillin-resistant pneumococci may be the etiologic organisms and, hence, should include a combination of third-generation cephalosporin (cefotaxime or ceftriaxone) and vancomycin.

Climo et. al., 1999 found that combinations of vancomycin and beta-lactams are synergistic against staphylococci with reduced susceptibilities to vancomycin. Evidence of synergism between combinations multiple antibacterial agents such as vancomycin and cephalosporins against 59 isolates of methicillin-resistant staphylococci (Staphylococcus aureus, Staphylococcus epidermidis, and Staphylococcus haemolyticus) was collected. They concluded that the combination of vancomycin and beta-lactams with antistaphylococcal activity is an effective regiment for the treatment of infections with clinical strains of staphylococci which demonstrate reduced susceptibility to glycopeptides.

In a study of antimicrobial resistance of invasive Streptococcus pneumoniae in Slovenia, 1993-1995, Cizman M et. al. (1997) found that all penicillin-resistant isolates (intermediate resistance) were susceptible to cefotaxime, ceftriaxone and vancomycin.

Disadvantages of Prior Art

One feature of the references stated above is that each drug of the combination used in the multiple antibacterial agent treatments reported therein was individually administered one after the other without specific or predetermined ratio. Such administration and also the co-administration as mentioned in case of some of the above references have a number of disadvantages. These are as stated here:

1. Drugs mentioned as the combinations used in the multiple drug treatment are administered one after the other.

2. These drugs are not available in a premixed compositions as single drug.

3. There is complexity involved in administration of the drug as more number of pricks is required and the time of administration is also long.

4. Treatment time is prolonged to about 14 days in case of individual administration of these drugs and to about 7 days in case of co-administration of the composition of invention.

5. Cost to the patient is higher due to increased hospitalization time.

6. The failure rate is higher due to inconsistency of dose. Kazragis et al (1996) have given ceftriaxone at a dose of 25 mg/kg of body weight administered every 12 h and Vancomycin at 30 mg/kg administered every 12 h; Ulla-Stina Salminen et. al. (1999) have given 2 g dosage of ceftriaxone and 500 mg of vancomycin iv every 6 h for 48 h.

7. Due to non availability of fixed dose at fixed intervals, chances of development of resistance are very high in case of prior art.

The individual administration of the Ceftriaxone and vancomycin components of drugs described in the prior art fails to solve the treatment problem satisfactorily because of following reasons:

(a). The components are administered one after the other and individually in different doses.

(b). The components are administered either in equal proportions or the ratio is undefined and not fixed.

(c). The success rate of such a treatment is not as per the desired levels.

(d). Use of oral route with parenteral route is adopted in some cases.

(e). Co-administration has to be done very carefully as two individual components are not chemically compatible with each other.

(f). Due to incompatibility of individual components more precautions are required to be taken like use of different syringes for individual component and difference in time of administration of two drugs.

Advantages of Invention

An essential requirement for successful antibacterial therapy is that drug must reach a site of infection at concentrations near or higher than the minimal inhibitory concentrations. Furthermore, these concentrations must be maintained for a certain minimal time as achieved by the composition of invention. The differences in the ability of various antibacterial agents to reach site of infection sometimes have greater influence on determining the agent for treatment than the differences in the agents' intrinsic antibacterial activity.

Parenteral administration is generally the preferred method of drug delivery in emergency situations, and is also useful in treating subjects with digestive tract illnesses or swallowing difficulties, as well as subjects who are uncooperative, unconscious, or otherwise unable or unwilling to accept oral medication.

Moreover, parenteral routes of administration offer numerous benefits over oral delivery in many situations, for a wide variety of drugs. One advantage of parenteral administration is that therapeutically effective blood serum concentrations of the drug are achieved in a shorter time than is achievable by other routes of administration. This results in more rapid onset of therapeutic action and more complete delivery to a site of infection, as compared with other routes of administration such as oral, transmucosal, transdermal, rectal and vaginal routes. This is especially true of intravenous injection, whereby the drug is placed directly in the bloodstream. Hence the present invention is developed in parenteral form only.

Parenteral administration can also result in more predictable blood serum concentrations of a drug than oral administration. This is because losses in the gastrointestinal tract due to metabolism, partial or total degradation of the drug, binding to food, and other causes are eliminated. In addition, the effective use of some antibacterial agents requires continuous, controlled administration to achieve the desired effect.

Another aspect of parenteral drug theory that has been considered hitherto is that the parenteral drug products should be inspected visually for particulate matter/precipitation and discoloration prior to administration, whenever possible. Although existing individual formulations exhibit satisfactory clarity when prepared in accordance with recommended manufacturer's instructions, it is mandatory to further reduce and minimize the particulate formations/precipitations that occur in the combining pharmaceutical compositions upon reconstitution as is done in prior art.

The above mentioned prior art references disclose a number of useful compositions. However, there still exists a need in the medical field for pharmaceutical compositions that use multiple antibacterial agents and also for methods of treatment and prevention for infective conditions, using such compositions that:

(a) ensure rapid delivery of therapeutic agent(s) to the site of an infective condition, (b) are safe and chemically compatible to each other (c) can be administered easily without posing any medical hazard, (d) provide effective treatment of the hospitalised patient for the treatment of bacterial infections and other complications associated with a non-ocular infective condition, (e) provide efficacy against a wide variety of infectious organisms, (f) have a potential to administer a lower dose of a therapeutic agent while still providing efficacy, and (g) have a potential to administer a higher dose of an antibacterial agent without increased side effects.

(h) ensure improvement of the therapeutic index of an active agent while decreasing its general toxicity and minimizing the risk of systemic effects.

Objects of the Invention

Accordingly, the objects of the present invention are described as below:

An object of the present invention is to provide pharmaceutical compositions that are safe, that have efficacy against a wide variety of infectious organisms, and to provide a composition that is useful in providing effective treatment against non-ocular infective conditions of a multi drug resistant bacteria.

Yet another object of the present invention is to provide a method of treatment of non-ocular infective conditions that ensures rapid therapeutic delivery of therapeutic agent(s) to the site of the infective condition.

Further object of the present invention is to provide pharmaceutically effective dose for parenteral administration for hospitalized patients with acute or serious non-ocular infections.

Still another object of the present invention is to provide dosage forms that have a potential to provide effective treatment without increased side effects.

A further objective of the present invention is to provide a process of making pharmaceutical compositions of the present invention.

A still further objective of the present invention is to provide a chemically compatible stable formulation that is easy to administer.

SUMMARY OF THE INVENTION

The invention describes a pharmaceutical composition to combat multiple-drug-resistant bacteria in non-ocular infective conditions. Compositions comprising glycopeptides, in particular vancomycin, and cephalosporins, in particular ceftriaxone, are disclosed. Such compositions are found to be useful for parenteral administration for hospitalized patients with serious infections. Specifically, this invention also discloses a pharmaceutical composition further including an excipient such as CVMC agent and is available in dry powder form for reconstitution before injection with a suitable solvent.

The pharmaceutical compositions of this invention have been found normally to enhance resistance to precipitation in solutions to be administered parenterally.

The invention also gives details of the dosage forms stored in sealed containers to be reconstituted before use. The invention further provides a process to manufacture these compositions and also a method of treating a subject having non-ocular infective conditions due to multi drug resistant bacteria.

DEFINITIONS

Some of the various terms used in the description of the invention are described below:

A "non-ocular infective condition" herein is a non-neoplastic disease, disorder or condition of a bodily tissue, organ or system other than an eye or part thereof, that is mediated by a pathogenic bacterium or that is otherwise responsive to treatment with the antibacterial agents such as glycopeptides and cephalosporins.

The term, "dose-concentrate" refers to a solution of the pharmaceutical composition. The dose-concentrate may be held in the container where it was formed by adding suitable solvent or diluent to the pharmaceutical composition. The dose-concentrate is generally further diluted to a unit dosage concentration for administration to a mammal. The entire volume of the dose-concentrate or aliquots thereof may be used in preparing unit dose(s) for treatment by the method of this invention.

The term "antibacterially effective amount" as used herein refers to an amount of both the antibacterial agents that is sufficient, when administered by the method of the invention, to reduce, relieve, prevent or delay onset of one or more symptoms of an infective condition being treated, or to reduce numbers and/or activity of a causal organism.

The term "treatment" herein includes administration parenterally to a subject that show clinical signs of a non-ocular infective condition, or at risk of developing such an infective condition.

The term "parenteral administration" herein embraces the means of injection or infusion of a composition into veins that is intravenously only. For example, administration can be by longer-term infusion. Any known device useful for parenteral infusion of a drug can be used to effect such administration. Parenteral administration herein does not include administration solely to the skin surface, such as topical or transdermal administration. Both the antibacterial agents are administered parenterally in the method of the invention. Preferred parenteral administration route is intravenous only.

DETAILED DESCRIPTION OF THE INVENTION

The present invention provides pharmaceutical compositions containing two antibacterial agents both acting as active ingredients, to combat non-ocular infective conditions corresponding to a single unit/multiple dose. The invention also discloses a method of treatment of non-ocular infective conditions using these compositions. The compositions and method of treatment described in the present invention are used against multiple-drug-resistant bacteria such as MRSA. The invention also provides a process of manufacturing these compositions. The invention further provides dosage forms stored in sealed containers.

Different embodiments of the present invention are described below.

The preferred embodiment of the present invention basically provides a composition that is parenterally administrable for combating multiple-drug resistant bacteria, comprising:

a. an antibacterially effective amounts of a first antibacterial agent such as a glycopeptide, wherein the glycopeptide is vancomydin, or a pharmaceutically acceptable salt thereof such as vancomycin hydrochloride, b. an antibacterially effective amount of a second antibacterial agent such as a cephalosporin wherein the cephalosporin is ceftriaxone or a pharmaceutically acceptable salt thereof such as ceftriaxone sodium.

Preferred antibacterial agents applicable for use according to the invention are beta-lactams and glycopeptides, but not limited to only beta-lactam antibacterials such as natural and synthetic penicillin type agents including penam penicillins (such as benzyl penicillin, phenoxymethyl penicillin, coxacillin, nafcillin, methicillin, oxacillin, amoxycillin, temocillin, ticarcillin and the like), penicillinase-stable penicillins, acylamino and carboxypenicillins (such as piperacillin, aziocillin, meziocillin, carbenicillin, temocillin, ticarcillin and the like), and broader spectrum penicillins (such as streptomycin, neomycin, framycetin, gentamicin, apramycin, amikacin, spectinomycin, amoxycillin, ampicillin and the like), cephalosporins (such as ceftriaxone, cefepime, ceftazidime, cefotaxime, cefuroxime and cefaclor) and glycopeptides (such as vancomycin, avoparcin, ramoplanin, teicoplanin and daptomycin and the like).

The antibacterial agents are administered simultaneously or sequentially in any order. The pharmaceutical composition according to the preferred embodiment of the invention is in the form of a sterile powder wherein said predetermined weight ratio of said first antibacterial agent to said second antibacterial agent is in the range from about 1:4 to about 4:1 respectively, preferably in the range from about 1:3 to about 3:1 respectively, more preferably in the range from about 1:2 to about 2:1 respectively that can be reconstituted by addition of a compatible reconstitution diluent prior to parenteral administration corresponding to a single unit/multiple dose.

Vancomycin hydrochloride is the most preferred form of vancomycin in the compositions of the present invention. Vancomycin free acid is the preferred source of vancomycin; produced by the growth of certain strain of Amycolatopsis orientalis (Nocardia orientalis, Streptomyces orientalis) or by any other means; for use in making the compositions of the present invention. The free acid may be converted to the hydrochloride salt during the formulation process. Vancomycin hydrochloride is $(S_a)$-(3S,6R,7R,22R,23S,26S,36R, 38aR)-44-{[2-O-(3-Amino-2,3,6-trideoxy-3-C-methyl-□-L-lyxo-hexopyranosyl)-□-D-glucopyranosyl]oxy}-3-(carbamoylmethyl)-10,19-dichloro-2,3,4,5,6,7,23,24,25,26, 36,37,38,38a-tetradecahydro-7,22,28,30,32-pentahydroxy-6-[(2R)-4-methyl-2-(methylamino)valeramido]-2,5,24,38, 39-pentaoxo-22H-8, 11:18,21-dietheno-23,36-(iminomethano)-13, 16:31,35-dimetheno-1H,16H-[1,6,9] oxadiazacyclohexadecino [4,5-m][10,2,16]-benzoxadiazacyclotetracosine-26-carboxylic acid, monohydrochloride with a chemical formula of $C_6H_{75}Cl_2N_9O_{24}$, HCl and a molecular weight of 1485.7

Ceftriaxone sodium is the most preferred form of ceftriaxone in the compositions of the present invention. Ceftriaxone free acid is the preferred source of ceftriaxone for use in making the compositions of the present invention. The free acid may be converted to the sodium salt during the formulation process. Ceftriaxone sodium is (Z)-7-[2-(2-Aminothiazole-4-yl)-2-methoxyiminoacetamido]-3-[(2,5-dihydro-6-hydroxy-2-methyl-5-oxo-1,2,4-triazin-3-yl)thiomethyl]-3-cephem-4-carboxylic acid, disodium salt, Sesquaterhydrate with a chemical formula of $C_{18}H_{16}N_8Na_2O_7S_3,3.5H_2O$ and a molecular weight of 661.6.

It has been found that incorporation of a chemical vector agent and a suitable salt thereof into the dry powder composition of the invention makes the combination stable after reconstitution. As a further embodiment of this invention, the composition of the preferred embodiment further comprises a stabilizing agent such as sodium bicarbonate or L-arginine wherein the weight of stabilizing agent, is in the range of about 35% to about 75% of the combined weight of said first antibacterial agent and said second antibacterial agent.

The pharmaceutical combination of the present invention is also presented in a reconstituted form along with a sterile solvent vehicle with or without, an excipient or a neutralizing agent.

The dosage form of the compositions of the present invention is parenteral. The total said dosage is administered preferably twice a day to a patient, spread over a period of 12 hours in a day depending upon the patient condition and severity of infection.

The antibacterial agents may be present in the composition as drug particles, powders, granules, nanoparticles, microparticulates, microspheres, in lyophilized form and the like.

The suitable solvent vehicle referred to in the invention is preferably aqueous based. The pharmaceutically acceptable carrier or vehicle referred to in this invention is one that has no unacceptably injurious or toxic effect on the subject when administered as a component of a composition by parenteral administration in an amount required herein. No excipient ingredient of such carrier or vehicle used in this invention reacts in a deleterious manner with another excipient or with the antibacterial agents in the composition.

The antibiotic product composition disclosed in the preferred embodiment of this invention is twice a day product, whereby the administration of the antibiotic product is a dose concentrate corresponding to a single unit/multiple dose and is diluted before administration in suitable infusions; such as Sterile suitable solvent, 0.9% Sodium Chloride, 5% Dextrose Injection. The preferred regimen is that the product is administered twice over a twelve hour period.

Particulate formation/precipitation inhibitor of the invention include ethylene diamine tetraacetic acid (EDTA) and salts thereof, a stabilizing agent such as sodium bicarbonate, a neutralizing agent, a buffer or a chemical vector. Preferably, the pharmaceutical compositions described herein have an effective amount of a particulate formation/precipitation inhibitor in the range of about 10% to 40% of the total weight of the combination product in the form of a chemical vector.

In another embodiment of the present invention the composition comprises a therapeutically effective amount of vancomycin or a pharmaceutically acceptable salt thereof such as vancomycin hydrochloride, wherein said first antibacterial agent (vancomycin hydrochloride) is present in said composition at a concentration in the range from about 1 mg/ml to about 100 mg/ml, preferably in the range from about 5 mg/ml to about 75 mg/ml, and more preferably in the range of about 10 mg/ml to about 50 mg/ml and ceftriaxone or a pharmaceutically acceptable salt thereof such as ceftriaxone sodium where in second antibacterial agent (ceftriaxone sodium) is present in said composition at a concentration in the range from about 1 mg/ml to about 200 mg/ml, preferably in the range from about 5 mg/ml to about 150 mg/ml, and more preferably in the range from about 10 mg/ml to about 100 mg/ml along with an effective amount of a particulate formation/precipitation inhibitor in the form of a suitable chemical vector which is reconstituted by addition of a sterile solvent vehicle. The pH of this embodiment may be maintained within a range of about 7.0 to 9.0.

The inventors have found that this composition advantageously overcomes the bacterial resistance that is experienced by the monotherapy described in the prior art. They have discovered that the glycopeptide component of the composition of the present invention provides a bactericidal action against a variety of gram positive bacteria, whereas the cephalosporin elements exhibit a high degree of stability in the presence of beta-lactamases of both gram positive and gram negative bacteria.

The present invention also provides a novel method of treatment of non-ocular infective conditions. The method comprises administering to a subject, by parenteral administration, the composition described in the preferred embodiment in combination therapy with a suitable solvent vehicle. The combination therapy thus described is administered to a subject who has clinical signs of an infective condition. Parenteral methods of administration are an important option for delivery of therapeutic agents especially for drugs like vancomycin which are poorly absorbed when administered orally, and to which bacterial resistance tends to develop in gastrointestinal tract. Ceftriaxone is also administered through intravenous route effectively.

Combination therapy refers to a treatment regimen wherein the two antibacterial agents are administered together in such a way as to provide a beneficial effect from co-action of these therapeutic agents. Such beneficial effect can include, but is not limited to, pharmacokinetic or pharmacodynamic co-action of the therapeutic agents. Combination therapy, for example, results in lowering the dosage of one or both agents than would normally be administered during monotherapy described in the prior art, thus decreasing risk or incidence of adverse effects associated with higher doses. Alternatively, combination therapy also results in increased therapeutic effect at the normal dose of each agent in monotherapy. Furthermore, combination therapy maximizes the therapeutic effect.

Combination therapy as referred to in this invention does not encompass administration of two or more therapeutic agents as part of separate monotherapy regimens that incidentally and arbitrarily result in sequential or simultaneous treatment.

They have also found that when administered intravenously, the combination therapy of the invention provides enhanced treatment options as compared to administration of either the antibacterial agent. Combination therapy according to the invention provides effective treatment of an infective condition, and reduces the time required to resolve the infective condition caused by bacteria particularly the multi-drug-resistant varieties such as MRSA and Staphylococcal species. It is found by the inventors that the method of treatment disclosed in this invention also reduces the risk of developing such infective conditions. Therefore the combination therapy as described herein can be administered prior to or following surgery or hospital admission to prevent or reduce the risk of a subject developing an infection caused mainly by MRSA and Staphylococcal species.

In another embodiment of the invention, the antibacterial agents applicable for use include any such agents that are effective for treatment and/or prevention of an infectious condition and/or complications associated therewith. The active ingredients used in the compositions of the present invention include any of the antibacterial agents mentioned above or their pharmaceutically acceptable tautomers, stereoisomers, enantiomers, salts, hydrates, dihydrates, and pro-drugs, and are not limited to any one form of the drug.

The inventors have found that the combination therapy as described herein provides safe, effective treatment for the infectious component of a non-ocular infective conditions such as meningitis; sepsis; typhoid; abdominal infections (peritonitis, infections of the biliary and gastrointestinal tracts); infections of the bones, joints, soft tissue, and wounds; infections in patients with impaired defense mechanisms; renal and urinary tract infections; respiratory tract infections, particularly pneumonia, and ear, nose and throat infections; genital infections, including gonorrhoea; lower respiratory tract infections; skin and skin structure infections; staphylococcal endocarditis. Inventors have also found that in such combination therapy both active ingredients can act synergistically in the presence of chemical vector for the treatment of complications associated with above described conditions.

This invention includes a sterile fixed dose combination available as dose concentrate of two antibacterial agents in antibacterially effective amount useful for treatment of non ocular bacterial infections in mammals which when reconstituted generally has reduced particulate formation/precipitation and is chemically compatible and stable.

When making the suitable solvent vehicle a neutralizing agent like aminocarboxylic acid chelating agent, for example ethylenediaminetetraacetic acid (EDTA), diethylenetriaminepentaacetic acid (DTPA), hydroxyethylenediaminetriaceti-c acid (HEDTA), nitrilotriacetic acid (NTA), is optionally mixed with a desired quantity of water for injection and neutralized with sodium bicarbonate or L-arginine or other suitable agents, to bring the concentration of the solution within the preferred range of about 10 to about 100 mg/ml, more preferably within the range of about 20 to about 90 mg/ml, and most preferably within the range of about 40 to about 80 mg/ml or any combination or sub combination of ranges therein.

In another embodiment of the present invention, a pharmaceutically effective unit/multiple dose of said antibiotic combination, in the form of dose concentrate, is provided in a sealed airtight container which is selected from the group consisting of a vial, an ampoule, a syringe, a packet, a pouch and an auto-injector, wherein said container has a head space volume sufficient for introduction of appropriate volume of a suitable solvent sufficient to form a unit/multiple dose in the form of an appropriate reconstituted solution of said antibiotic combination.

The head space volume is occupied aseptically by an inert-gas-limited micro atmosphere, which comprises essentially one or more inert gas which is selected from the group of noble gases and nitrogen; preferably nitrogen, volume of said nitrogen gas being not more than 5% of said head space volume, and wherein ratio of said fill volume to said head space volume is not less than 1:1.

In the present invention, the antibiotic combination is alternatively provided in a sealed container such as transparent glass vial capped with appropriate halogenated stopper and seal, and is used after reconstitution for intravenous administration for the treatment of non ocular bacterial infections caused by multi drug resistant bacteria.

According to this invention, the process for the manufacture of a pharmaceutical composition as a dose-concentrate in the powder form contained in sealed container that can be reconstituted prior to administration, comprises the steps of: (a) sterile filling/blending two active ingredients, first active ingredient being the vancomycin or the pharmaceutically acceptable salt thereof and second ingredient being the ceftriaxone or the pharmaceutically acceptable salt thereof, adding a particulate formation/precipitation inhibitor present in the form of chemical vector; the sterile filling/blending being continued for a period ranging from about 1 hour to about 8 hours, (b) proportioning the sterile fill/blend of step (a), aseptically to get desired dose in weight ratio of said first active ingredient to said second active ingredient in the range from about 4:1 to about 1:4 respectively, preferably from about 3:1 to about 1:3 respectively, more preferably in the range of about 2:1 to about 1:2 respectively, with the range of chemical vector being 10% to 40% of the total weight of blended/filled composition and (c) capping aseptically with pre or post inert gassing.

Sterilization of the liquid solvent vehicle of the invention can be achieved by any conventional method that preserves the biological activity of the composition, such as by filter sterilization, moist heat or steam heat sterilized.

Conditions that can be treated and/or prevented by the method of the invention include, but are not limited to, disorders caused by gram positive organisms such as Staphylococcus, Micrococcus, Streptococcus, Enterococcus, Leuconostoc, Pediococcus, Stomatococcus, coryneform bacteria, Listerla, Erysipelothrix, Kurthia, Bacillus, Nocardia, Rhodococcus, Gordona, Actinomadura, Streptomyces, Mycobacterium, Colostridium, Peptostreptococcus, Propionibacterum, Lactobacllus, Actinomyces and the like; gram negative organisms such as Enterobacteriaceae, Escherichia, Shigella, Salmonella, Klebsiella, Enterobacter, Citrobacter, Serratia, Yersinia, Vibrio, Aeromonas, Plesiomonas, Pseudomonas, Burkholderia, Stenotrophomonas, Ralstonia, Brevundimonas, Comamonas, Acidovorax, Acinetobacter, Achromobacter, Alcaligenes, Moraxella, Methylobacterium, Actinobacllus, Capnocytophaga, Eiknella, Kingella, Legionella, Neisseria, Branhamella, Haemophilus, Bordetella, Brucella, Pasteurella, Bartonella, Afipia, Francisella, Bacteroides, Porphyromonas, Prevotella, Fusobacterium, Campylobacter, Arcobacter, Helicobacter, Leptospira, Leptonema, Chlamydia, Rickettsia, Coxiella, Ehrlichia and the like; and other infective organisms including Treponema, spiochetes, Borrelia, Mycoplasma, Ureaplasma, obligate intercellular bacteria and Anaerobic organisms: Bacteroides spp. (bile-sensitive)*, Clostridium spp. (excluding C. diffcile), Fusobacterium nucleatum, Fusobacterium spp. (other), Gafflkia anaerobica (formerly Peptococcus), Peptostreptococcus spp. and the like.

Infective conditions for which the method of the invention is useful include, without limitation, bacterial meningitis, soft tissue infections, infections of the respiratory system including lower respiratory tract infections, sinusitis, otolaryngological infections, infections of the gastrointestinal tract (such as gastroenteritis, helicobacter pylori, bacterial diarrhea, bacillary dysentery, extraintestinal infections, intestinal yersiniosis, enteritis, terminal ileitis, peptic ulcer disease, gastric ulcer disease, atrophic gastritis, mesenteric lymphadenitis, pseudoappendicitis and the like); infection related to abdominal trauma; pyelonephritis; nocardial pulmonary infections (such as pleural effusion, pericarditis, mediastinitis, superior vena cava obstruction and the like); cutaneous nocardiosis (such as mycetoma, lymphocutaneous infections and the like), skin infections (such as impetigo, erysipelas, cellulitis, skin ulcers, secondary cutaneous involvement with disseminated disease and the like, scalded skin syndrome); leprosy, mycobacterial lymphadenitis, kidney infections, malacoplakia, puerperal sepsis, bloodstream infections (such as typhoid and the like), anthrax, plagues (such as bubonic plague, pneumonic plague, primary and secondary septicemic plague and the like); scarlet fever, rheumatic fever, cholera, Haverhill fever, Potomac fever, brucellosis, Carrion's disease, trench fever, bacillary epithelioid angiomatosis, leptospirosis, Lyme disease, rickettsiosis, Q fever, human monocytotropic ehrlichiosis, cat scratch disease, tularemia, pseudo-infections, legionellosis, noscoccomial infections (such as furuncles, postoperative wound infections of various sites and the like), erysipeloid, osteomyehtis, prostatitis, peritonitis, encephalitis, cerebrospinal infections, infection of cerebrospinal fluid shunt, meningoencephalitis, infection of the joints, prosthetic joint infections, septic arthritis, myonecrosis, echyma gangrenosum, cholecystitis, melioidosis, mastoiditis, epididymitis, bursitis, comamonas testosteroni infections, mastitis, cerebritis, abscesses (of muscle, urogenital tract, central nervous system, intra-abdominal, intracranial and the like), reproductive tract infections (such as vaginal infections, cervical lymphadenitis, gonorrhea, urethritis, endometritis, postpartum endometritis, perihepatitis, Chlamydia trachomatis infections, pelvic inflammatory disease, endocervical infections, salpingitis, pelvic peritonitis, tubo-ovarian abscesses, chancroid, amnionitis, chorioamnionitis, treponematosis and the like), infections in patients with impaired defense mechanisms.

Experimental Data:

Experimental data in support of the compositions and methods of treatment proposed in this invention is presented below. It comprises data on minimum inhibitory concentration, bacterial susceptibility tests, stability and cost comparison. Results are presented in Tables 1, 2 and 3.

Minimum Inhibitory Concentration Data

Average MIC data with growth details in various concentration of ceftriaxone and vancomycin combination of the present invention, ceftriaxone alone and vancomycin alone with following bacteria such as MSSA, Enterococcus, S. pneumoniae, Penicillin resistant streptococcus pneumoniae, MRSA. The observation for the combination of ceftriaxone and vancomycin used were successful in inhibiting bacteria in lesser concentration than any of the salts alone, in wide range of bacteria as shown in table below.

Bacterial Susceptibility Test

Bacterial susceptibility test was performed for ceftriaxone and vancomycin, ceftriaxone alone and vancomycin alone on different microorganisms. Different concentrations were selected mentioned to as highest, high, low and lowest in data. Zone size was determined in mm. The activity of ceftriaxone and vancomycin was best seen in E. coli, B. subtillis, Klebsiella pneumoniae, Strptococus pneumoniae, and enterococus faecalis. The activity of combination observation was more potent than single salt.

Stability Data

Stability study was done for ceftriaxone and vancomycin combination of present invention for 6 months. All procedures were carried as per standard testing procedures. It has been observed that the product is stable under accelerated conditions for 6 months.

TABLE 1

Average MIC data

| Concentrations (μg/ml) | Drag | S. aurens (MRSA) | Enterococcus | S. pneumoniae | Streptococcus pneumoniae | S. aurens |
|---|---|---|---|---|---|---|
| 128 | Ceftriaxone | No growth | No growth | No growth | No growth | No growth |
|  | Vancomycin | No growth | No growth | No growth | No growth | No growth |
|  | Combination | No growth | No growth | No growth | No growth | No growth |
| 64 | Ceftriaxone | No growth | No growth | No growth | No growth | No growth |
|  | Vancomycin | No growth | No growth | No growth | No growth | No growth |
|  | Combination | No growth | No growth | No growth | No growth | No growth |
| 32 | Ceftriaxone | Growth Found | No growth | No growth | No growth | No growth |
|  | Vancomycin | No growth | No growth | No growth | No growth | No growth |
|  | Combination | No growth | No growth | No growth | No growth | No growth |
| 16 | Ceftriaxone | Growth Found | No growth | No growth | No growth | No growth |
|  | Vancomycin | No growth | No growth | No growth | No growth | No growth |
|  | Combination | No growth | No growth | No growth | No growth | No growth |
| 8 | Ceftriaxone | Growth Found | No growth | No growth | No growth | No growth |
|  | Vancomycin | No growth | No growth | No growth | No growth | No growth |
|  | Combination | No growth | No growth | No growth | No growth | No growth |
| 4 | Ceftriaxone | Growth Found | No growth | No growth | No growth | No growth |
|  | Vancomycin | No growth | No growth | No growth | No growth | No growth |
|  | Combination | No growth | No growth | No growth | No growth | No growth |
| 2 | Ceftriaxone | Growth Found | No growth | No growth | Growth Found | No growth |
|  | Vancomycin | Growth Found | No growth | No growth | No growth | Growth Found |
|  | Combination | No growth | No growth | No growth | No growth | No growth |
| 1 | Ceftriaxone | Growth Found | No growth | No growth | Growth Found | No growth |
|  | Vancomycin | Growth Found | No growth | No growth | No growth | Growth Found |
|  | Combination | Growth Found | No growth | No growth | No growth | No growth |
| 0.5 | Ceftriaxone | Growth Found | Growth Found | No growth | Growth Found | Growth Found |
|  | Vancomycin | Growth Found | No growth | No growth | Growth Found | Growth Found |
|  | Combination | Growth Found | No growth | No growth | No growth | No growth |
| 0.25 | Ceftriaxone | Growth Found | Growth Found | Growth Found | Growth Found | Growth Found |
|  | Vancomycin | Growth Found | Growth Found | Growth Found | Growth Found | Growth Found |
|  | Combination | Growth Found | No growth | No growth | Growth Found | Growth Found |
| 0.125 | Ceftriaxone | Growth Found | Growth Found | Growth Found | Growth Found | Growth Found |
|  | Vancomycin | Growth Found | Growth Found | Growth Found | Growth Found | Growth Found |
|  | Combination | Growth Found | Growth Found | Growth Found | Growth Found | Growth Found |

TABLE 2

STABILITY STUDY
Name of product: Ceftriaxone & vancomycin for injection. 1.5 g

| Period (months) | Storage condition | Description | Identification | Particulate matter | BET | Sterility | PH(7.0-10.0) | Assay 90-110% of labelled amount of Ceftriaxone | Assay 90-110% of labelled amount of Vancomycin |
|---|---|---|---|---|---|---|---|---|---|
| Initial | — | Almost white colored powder | Passes test | Passes test | Passes test | Passes test | 8.85 | 100.3 | 99.7 |
| 1 | 40° C./75% RH | Almost cream colored powder | Passes test | Passes test | Passes test | Passes test | 8.80 | 99.8 | 99.1 |
| 2 | 40° C./75% RH | A cream colored powder | Passes test | Passes test | Passes test | Passes test | 8.76 | 99.1 | 98.3 |
| 3 | 40° C./75% RH | A cream colored powder | Passes test | Passes test | Passes test | Passes test | 8.70 | 98.4 | 97.5 |
| 6 | 40° C./75% RH | A dark cream colored powder | Passes test | Passes test | Passes test | Passes test | 8.62 | 97.4 | 96.6 |

Packaging: glass vial

TABLE 3

Average cost comparison of Prior art v/s invention

| Prior art | Invention | Cost Saved |
| --- | --- | --- |
| Average hospitalization time 14 days @ Rs-1000/day = Rs-14000/- Average cost of Vancomycin 1 g @ Rs-750/- bd for 14 days and Ceftriaxone 2 g @ bd for 14 days = 750 × 2 × 14 = Rs-21000/- + 115 × 2 × 14 = Rs-3220/- Total cost = Rs-24,220/- | Average hospitalization time 7 days @ Rs-1000/day = Rs-7000/- Average cost of Vancomycin Ceftriaxone@ Rs-700/-bd for 7 days = 700 × 2 × 7 = Rs-9800/- Total cost = Rs-9800/- | Rs-7000/- per hospital admission Rs-14,420/- per treatment cost |

Net saving to the patient per treatment is Rs-21,420/-

While the above description contains many specificities, these should not be construed as limitations in the scope of the invention but as exemplifications of embodiments thereof. Many other variations are possible. Accordingly, the scope of the invention should be determined not by the embodiments illustrated, but by the appended claims and their legal equivalents.

The invention claimed is:

1. An antibiotic pharmaceutical composition suitable for parenteral injection, comprising:
   a) a cephalosporin selected from the group consisting of cephazoline, cefuroxime, cefotaxime, cefpirome, cefepime, cefriaxone, ceftazidime and cefoperazone;
   b) a glycopeptide selected from the group consisting of Avoparcin, Ramoplanin, Vancomycin, Telcoplanin, and Daptomycin; and
   c) an aqueous solvent vehicle comprising a compatibility/stabilizing agent selected from the group consisting of L-arginine, L-lysine, and L-histidine,
   wherein said cephalosporin and said glycopeptide are present in a single premix form in a weight ratio ranging from 1:4 to 4:1.

2. The composition of claim 1 wherein:
   a) glycopeptide selected from the group consisting of Avoparcin, Ramoplanin, Vancomycin, Telcoplanin, and Daptomycin;
   b) the cephalosporin is selected from the group consisting of cephazoline, cefuroxime, cefotaxime, cefpirome, cefepime, ceftriaxone, ceftazidime and cefoperazone; and
   c) the compatibility/stability agent is L-arginine.

3. The composition of claim 2 wherein:
   a) the glycopeptide is vancomycin or a pharmaceutically acceptable salt thereof and is present in an amount ranging from 1 to 100 mg/ml calculated as vancomycin crystalline free acid;
   b) the cephalosporin is ceftriaxone or a pharmaceutically acceptable salt thereof and is present in an amount in the ranging from 1 to 100 mg/ml calculated as ceftriaxone crystalline free acid; and
   c) the compatibility/stabilizing agent is in a weight ratio of 10%-45% of the total weight of the mixture.

4. A method of treating a non-ocular bacterial infection caused by a drug-resistant bacterium, comprising administering the pharmaceutical composition of claim 1 to a patient in need of treatment thereof.

5. The method of claim 4, wherein the glycopeptide is vancomycin or a pharmaceutically acceptable salt thereof.

6. The method of claim 4, wherein said cephalosporin is ceftriaxone.

7. The method of claim 4, wherein the pharmaceutical composition further comprises one or more excipients selected from the group consisting of diluents, antioxidants, preservatives, stabilizers, thickening agents, suspending agents, dispersing agents, solubilization agents, isotonic agents, buffering agents, wetting agents, lubricants, emulsifiers, salts, coloring agents, alcohols, and surfactants.

8. The method of claim 4, wherein the composition further comprises a particulate formation inhibitor is selected from the group consisting of ethylenediaminetetraacetic acid (EDTA), diethylenetriaminepentaacetic acid (DTPA), hydroxyethylenediaminetriaceti-c acid (HEDTA), and nitrilotriacetic acid (NTA).

9. The method of claim 8, wherein the EDTA is present in an amount ranging from 10 to 100 mg/ml.

10. The method of claim 4, wherein the compatibility/stabilizing agent is L-arginine.

11. The method of claim 4, wherein the pharmaceutical composition is in the form of a sterile powder, and wherein the sterile powder is reconstituted prior to administration by adding the pharmaceutically acceptable carrier for a parenteral administration.

12. The method of claim 4, wherein the bacteria responsible for the infection being treated is:
   a) a gram positive organism selected from the group consisting of *Staphylococcus, Micrococcus, Streptococcus, Enterococcus, Leuconostoc, Pediococcus, Stomatococcus, coryneform bacteria, Listerla, Erysipelothrix, Kurthia, Bacillus, Nocardia, Rhodococcus, Gordona, Actinomadura, Streptomyces, Mycobacterium, Colostridium, Peptostreptococcus, Propionibacterum, Lactobacllus*, and *Actinomyces*,
   b) a gram negative organism selected from the group consisting of Enterobacteriaceae, *Escherichia, Shigella, Salmonella, Klebsiella, Enterobacter, Citrobacter, Serratia, Yersinia, Vibrio, Aeromonas, Plesiomonas, Pseudomonas, Burkholderia, Stenotrophomonas, Ralstonia, Brevundimonas, Comamonas, Acidovorax, Acinetobacter, Achromobacter, Alcaligenes, Moraxella, Methylobacterium, Actinobacllus, Capnocytophaga, Eiknella, Kingella, Legionella, Neisseria, Branhamella, Haemophilus, Bordetella, Brucella, Pasteurella, Bartonella, Afipia, Francisella, Bacteroides, Porphyromonas, Prevotella, Fusobacterium, Campylobacter, Arcobacter, Helicobacter, Leptospira, Leptonema, Chlamydia, Rickettsia, Coxiella*, and *Ehrlichia*,
   c) an organism selected from the group consisting of *Treponema, Spirochetes, Borrelia, Mycoplasma, Ureaplasma*, and obligate intercellular bacteria, or
   d) an anaerobic organism selected from the group consisting of bile-sensitive *Bacteroides* spp., *Clostridium* spp., *Fusobacterium nucleatum, Fusobacterium* spp., *Gafflkia anaerobica*, and *Peptostreptococcus* spp.

13. The method of claim 4, wherein the bacteria are selected from the group consisting of *Staphalococcus aureus*, Methicillin-resistant *Staphylococcus aureus*, Multi Drug Resistant Bacteri, *Haemophilus influenzae, Neisseria gonorrhoeaea, N. meningitis, Staph. Epidermidis*, pneumococci, *Streptococcus mitis, Enterococcus faecalis, Streptococcus pneumoniae, Staphylococcus haemolyticus*.

14. The method of claim 4, wherein the bacterial infection being treated is selected from the group consisting of meningitis; sepsis; typhoid; abdominal infections; infections of the bone infections, joint infections, soft tissue infections, wounds; infections in patients with impaired defense mechanisms; renal infections, urinary tract infections; respiratory tract infections, ear, nose and throat infections; genital infections, lower respiratory tract infections; skin and skin structure infections; and staphylococcal endocarditis.

15. The method of claim 4, wherein the bacterial infection being treated is selected from the group consisting of bacterial meningitis, soft tissue infections, respiratory system infections, gastrointestinal infections; infections related to abdominal trauma; pyelonephritis; nocardial pulmonary infections; cutaneous nocardiosis, skin infections; leprosy, mycobacterial lymphadenitis, kidney infections, malacoplakia, puerperal sepsis, bloodstream infections, anthrax, plagues; scarlet fever, rheumatic fever, cholera, Haverhill fever, Potomac fever, brucellosis, Carrion's disease, trench fever, bacillary epithelioid angiomatosis, leptospirosis, Lyme disease, rickettsiosis, Q fever, human monocytotropic ehrlichiosis, cat scratch disease, tularemia, pseudo-infections, legionellosis, noscoccomial infections, erysipeloid, osteomyehtis, prostatitis, peritonitis, encephalitis, cerebrospinal infections, infection of cerebrospinal fluid shunt, meningoencephalitis, joint infections, prosthetic joint infections, septic arthritis, myonecrosis, echyma gangrenosum, cholecystitis, melioidosis, mastoiditis, epididymitis, bursitis, comamonas testosteroni infections, mastitis, cerebritis, abscesses, reproductive tract infections, and infections in patients with impaired defense mechanisms.

16. The method of claim 4, wherein said cephalosporin and glycopeptide are ceftriaxone and vancomycin, and pharmaceutically acceptable salts thereof, and the bacterial infection being treated results from a bacteria selected from the group consisting of *E. coli, B. subtillis, Klebsiella pneumoniae, Strptococus pneumoniae*, and *Enterococus faecalis*.

* * * * *

UNITED STATES PATENT AND TRADEMARK OFFICE
CERTIFICATE OF CORRECTION

PATENT NO.        : 8,778,873 B2                                              Page 1 of 1
APPLICATION NO.   : 13/095665
DATED             : July 15, 2014
INVENTOR(S)       : Chaudhary It is certified that error appears in the above-identified patent and that said Letters Patent is hereby corrected as shown below:

In the Claims

Claim 1, Column 15, line 30: "cefriaxone" should be --ceftriaxone--.

Claim 8, Column 16, line 9: "inhibitor is selected" should be --inhibitor selected--.

Claim 12, Column 16, line 34: "Enterobacteriaceae" should be --*Enterobacteriaceae*--.

Signed and Sealed this
Thirtieth Day of September, 2014

Michelle K. Lee
*Deputy Director of the United States Patent and Trademark Office*